US006630155B1

(12) United States Patent
Chandrashekar et al.

(10) Patent No.: US 6,630,155 B1
(45) Date of Patent: *Oct. 7, 2003

(54) CONTROLLED RELEASE LIQUID DELIVERY COMPOSITIONS WITH LOW INITIAL DRUG BURST

(75) Inventors: Bhagya L. Chandrashekar, Fort Collins, CO (US); Mingxing Zhou, Fort Collins, CO (US); Eileen M. Jarr, Fort Collins, CO (US); Richard L. Dunn, Fort Collins, CO (US)

(73) Assignee: Atrix Laboratories, Inc., Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/643,289

(22) Filed: Aug. 22, 2000

Related U.S. Application Data

(63) Continuation of application No. 09/181,355, filed on Oct. 28, 1998, now Pat. No. 6,143,314.

(51) Int. Cl.⁷ .................................................. A61F 2/00
(52) U.S. Cl. ...................... 424/426; 424/422; 424/423; 424/424; 424/425; 514/772.1
(58) Field of Search ................................ 424/422, 423, 424/424, 425, 426; 514/772.1

(56) References Cited

U.S. PATENT DOCUMENTS

| 4,938,763 | A | | 7/1990 | Dunn et al. ............... 604/891.1 |
|---|---|---|---|---|
| 5,278,201 | A | | 1/1994 | Dunn et al. ................. 523/113 |
| 5,278,202 | A | | 1/1994 | Dunn et al. ................. 523/113 |
| 5,780,044 | A | * | 7/1998 | Yewey et al. ............... 424/426 |
| 5,945,115 | A | * | 8/1999 | Dunn et al. ................. 424/422 |
| 6,395,293 | B2 | * | 5/2002 | Polson et al. ............... 424/426 |

FOREIGN PATENT DOCUMENTS

| EP | 0430474 A | 11/1989 | ............ A61K/9/70 |
|---|---|---|---|
| EP | 0539751 A | 10/1991 | ............ A61K/9/00 |
| WO | 90/03768 | 4/1990 | ............ A61E/2/00 |
| WO | 95/35097 | 6/1994 | ............ A61K/9/16 |
| WO | WO95/27481 | 10/1995 | ............ A61K/9/22 |

OTHER PUBLICATIONS

Jarr, E.M., et al., "Sustained Release of Lidocaine from an Injectable Implant System for Treatment of Post–Operative Pain", *Proceedings of the International Symp. control Rel. Bioact. Mater, 26*, pp. 631–632, (Jul. 1999).

* cited by examiner

*Primary Examiner*—Thurman K. Page
*Assistant Examiner*—Liliana Di Nola-Baron
(74) *Attorney, Agent, or Firm*—Schwegman, Lundberg, Woessner & Kluth, P.A.

(57) ABSTRACT

The invention provides a controlled release polymeric composition which includes a base polymer or copolymer, an organic solvent, a polymeric controlled release additive, and a biologically active agent. The polymeric controlled release additive reduces the initial burst of biologically active agent released from the polymeric composition as it is solidifying to form the solid implant. The controlled release additive is preferably a poly(lactide-co-glycolide)/polyethylene glycol block copolymer.

13 Claims, No Drawings

CONTROLLED RELEASE LIQUID DELIVERY COMPOSITIONS WITH LOW INITIAL DRUG BURST

This is a continuation of application Ser. No. 09/181,355, filed Oct. 28, 1998, now U.S Pat. No. 6,143,314.

BACKGROUND OF THE INVENTION

A variety of approaches have been developed to permit controlled, sustained release of a biologically active agent into a subject. Examples of controlled release systems include the polymeric compositions described in U.S. Pat. Nos. 4,938,763; 5,278,201 and 5,278,202. The compositions described in these patents are administered to the body of a subject in a flowable state. Once in the body, the composition coagulates or cures to form a solid implant.

One polymeric composition includes a thermoplastic polymer or copolymer, an organic solvent and a biologically active agent. The thermoplastic polymer is biocompatible, biodegradable and substantially insoluble in aqueous body or tissue fluids. The organic solvent is also biocompatible and miscible to dispersible in aqueous body or tissue fluids. The polymeric composition is flowable and can be introduced into the body using a syringe, for example. When the polymeric composition comes into contact with an aqueous medium. such as body or tissue fluid, the solvent dissipates or diffuses into the aqueous medium. Concurrently, the substantially insoluble thermoplastic polymer precipitates or coagulates to form a solid implant. As the thermoplastic polymer precipitates or coagulates to form the solid matrix, the active agent is trapped or encapsulated throughout the polymeric matrix. The biologically active agent is then released by dissolution or diffusion through the polymeric matrix and/or the biologically active agent is released as the matrix biodegrades.

However, the formation of the solid matrix from the flowable delivery system is not instantaneous. Typically the process can occur over a period of minutes to several hours. During this period, the rate of diffusion of the biologically active agent from the coagulating polymeric composition may be much more rapid than the rate of release that occurs from the subsequently formed solid matrix. This initial "burst" of biologically active agent that is released during implant formation may result in the loss or release of a large amount of the active agent. If the active agent is particularly toxic, this initial release or burst is likely to lead to toxic side effects and may damage adjacent tissues.

Therefore, a flowable delivery system that allows for the in situ formation of an implant while reducing or eliminating the initial "burst effect" would represent a significant advancement. Such delivery systems would permit higher concentrations of an active agent to be safely incorporated into an implant. The efficacy of such systems would also be improved, since a much greater percentage of the active agent would remain in the implant for sustained release and not be lost during the initial burst.

SUMMARY OF THE INVENTION

The invention is directed to a polymer composition which includes a base polymer that is a pharmaceutically acceptable, biocompatible, biodegradable and/or bioerodible, thermoplastic polymer or copolymer which is substantially insoluble in an aqueous medium; a pharmaceutically-acceptable, organic solvent that is miscible to dispersible in an aqueous medium; a biologically active agent; and a polymeric controlled release additive.

Preferably, the controlled release additive is a poly(lactide-co-glycolide)/polyethylene glycol (PLG/PEG) block copolymer. When brought in contact with an aqueous enviroment, such as body or tissue fluids which typically surround tissues or organs in an organism, the organic solvent dissipates or disperses into the aqueous or body fluid. Concurrently, the substantially insoluble thermoplastic base polymer precipitates or coagulates to form a solid matrix or implant. The biologically active agent is trapped or encapsulated within the polymeric matrix as the implant solidifies. The polymeric controlled release additive reduces the initial burst of biologically active agent released from the polymeric composition as it is solidifying to form the solid implant. Once the solid implant is formed, the biologically active agent is released from the solid matrix by diffusion or dissolution from within the polymeric matrix and/or by the degradation of the polymeric matrix.

The invention is also directed towards methods of using the controlled release composition.

DETAILED DESCRIPTION OF THE INVENTION

Definitions

As used herein, the term "tissue site" includes any tissues in an organism. A tissue site is typically surrounded by an aqueous or body fluid such as interstitial fluid, blood, serum, cerebrospinal fluid or peritoneal fluid.

The term "tissue defect" is a subset of "tissue site" and includes tissues, such as abraded tissue, traumatized tissue, a surgical incision or surgically resected tissue. Examples of tissue defects include, but are not limited to, surgical incisions in an internal organ such as an ovary, heart, liver, intestine, stomach, etc.

The term "biodegradable" means that the polymer and/or polymer matrix of the film will degrade over time by the action of enzymes, by hydrolytic action and/or by other similar mechanisms in the human body. By "bioerodible," it is meant that the film matrix will erode or degrade over time due, at least in part, to contact with substances found in the surrounding tissue fluids or cellular action. By "bioabsorbable," it is meant that the polymer matrix will be broken down and absorbed within the human body, for example, by a cell or tissue. "Biocompatible" means that neither the polymer, the solvent nor the resulting implant cause substantial tissue irritation or necrosis at the tissue site.

"Flowable" means that the polymer formulation is easy to manipulate and may be shaped and molded within the tissue site as it coagulates. Flowable includes formulations with a low viscosity or water-like consistency to those with a high viscosity, such as a paste-like material. Advantageously, the flowability of the polymer formulation allows it to conform to irregularities, crevices, cracks, and/or holes in the tissue site.

"Substantially insoluble" in an aqueous medium means that the thermoplastic polymer does not dissolve in an aqueous medium.

"Soluble" in an organic solvent means that the thermoplastic polymer dissolves at a concentration of about 10% to about 70% by weight in an organic solvent.

"Initial burst" or "Burst effect" refers to the release of a biologically active agent from the polymeric composition during the first 24 hours after the polymeric composition is contacted with an aqueous fluid. The "Burst effect" is believed to be due to the increased release of biologically active agent from the polymeric composition while it is coagulating to form a solid implant and still in a flowable state.

The present invention relates to an in situ forming biodegradable implant useful as a delivery system for a biologically active agent to adjacent or distant tissues and organs in an animal. The polymer composition of the invention includes a base polymer that is a pharmaceutically acceptable, biocompatible, biodegradable and/or bioerodible, thermoplastic polymer or copolymer which is substantially insoluble in an aqueous medium; a pharmaceutically-acceptable, organic solvent that is miscible to dispersible in an aqueous medium; a polymeric controlled release additive; and a biologically active agent. Preferably, the controlled release additive is a poly(lactide-co-glycolide)/polyethylene glycol (PLG/PEG) block copolymer.

When brought in contact with an aqueous environment, such as body or tissue fluids which typically surround tissues or organs in an organism, the organic solvent dissipates or disperses into the aqueous or body fluid. Concurrently, the substantially insoluble thermoplastic base polymer precipitates or coagulates to form a flexible matrix or film which traps or encapsulates the biologically active agent. The polymeric controlled release additive reduces the initial burst of biologically active agent released from the polymeric composition as it coagulates to form a solid implant. Because the polymeric controlled release additive is also a thermoplastic polymer, it too, coagulates to form a part of the matrix. Once the solid implant is formed, the biologically active agent is released from the implant by diffusion or dissolution from within the polymeric matrix and/or the biologically active agent is released as the matrix is biodegraded, bioeroded or bioabsorbed.

Thermoplastic Polymers.

Thermoplastic polymers useful as base polymers in the polymeric composition include pharmaceutically acceptable polymers that are biodegradable, bioabsorbable, and/or bioerodible. The thermoplastic polymers are capable of substantially dissolving in a water-soluble carrier, or solvent, to form a solution. Examples of suitable biodegradable polymers include, polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids) and copolymers, terpolymers and combinations thereof. Preferred thermoplastic polymers are polylactides, polyglycolides, polycaprolactones, polyanhydrides, and polyorthoesters.

The inherent viscosity (abbreviated as "I.V."; units are in deciliters/gram) of the thermoplastic polymer is a measure of its molecular weight and degradation time (e.g., a thermoplastic polymer with a high inherent viscosity has a higher molecular weight and longer degradation time). Typically, a thermoplastic polymer with a high molecular weight provides a stronger matrix and the matrix takes more time to degrade. In contrast, a thermoplastic polymer with a low molecular weight degrades more quickly and provides a softer matrix. Preferably, the thermoplastic polymer has a molecular weight, as shown by the inherent viscosity, from about 0.10 dL/g to about 1.2 dL/g (as measured in chloroform), more preferably from about 0.10 dL/g to about 0.40 dL/g.

The molecular weight of the thermoplastic polymer can be varied by many methods known in the art. The choice of method is typically determined by the type of polymer. For example, the degree of polymerization can be controlled by varying the amount of initiator and/or reaction time.

Suitable thermoplastic polymers are soluble in an organic solvent. The solubility of a thermoplastic polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric composition which includes a high molecular weight polymer tends to coagulate or solidify more quickly than a polymeric composition which includes a low-molecular weight polymer. Polymeric formulations which include high molecular weight polymers also tend to have a higher solution viscosity than a polymeric composition which includes a low-molecular weight polymer.

The viscosity of the flowable polymeric composition can vary from low viscosity, similar to that of water, to a high viscosity, similar to that of a paste, depending on the molecular weight and concentration of the thermoplastic polymer used in the composition. The viscosity can be varied such that the polymeric composition can be applied to a patient s tissues by any convenient technique, for example, by brushing, spraying, extruding. dripping, injecting, or painting. Different viscosities of the polymeric composition are preferable depending on the technique used to apply the composition. For example, spraying, via aerosolization, requires a polymeric composition having a low viscosity. In contrast, a polymeric composition with a higher viscosity may be desirable for other application techniques, for example, a polymeric composition having a putty-like consistency may be more preferable for bone regeneration applications. Typically, the polymeric composition includes about 10 wt % to about 80 wt %, more preferably about 30 wt % to about 60 wt % of a thermoplastic polymer.

Organic Solvents

Suitable organic solvents are those that are biocompatible, pharmaceutically acceptable, and miscible to dispersible in aqueous or body fluids. The organic solvent is capable of diffusing, dispersing, or leaching from the composition in situ into aqueous tissue or body fluid of the implant site, such as blood, serum, lymph, cerebral spinal fluid (CSF), or saliva.

Examples of suitable solvents include substituted heterocyclic compounds such as N-methyl-2-pyrrolidone (NMP), 2 pyrrolidone; esters of carbonic acid and alkyl alcohols such as propylene carbonate, ethylene carbonate and dimethyl carbonate; alkyl esters of mono-, di-, and tricarboxylic acids such as 2-ethyoxyethyl acetate, ethyl acetate, methyl acetate, ethyl lactate, ethyl butyrate, diethyl malonate, diethyl glutonate, tributyl citrate, diethyl succinate, tributyrin, isopropyl myristate, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; alcohols such as solketal, glycerol formal, and glycofurol; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and mixtures and combinations thereof. Preferred solvents include N-methyl-2-pyrrolidone, 2-pyrrolidone, dimethylsulfoxide, ethyl lactate, and propylene carbonate, solketal, glycerol formal, and glycofurol.

Typically, the polymeric composition includes about 20 wt % to about 90 wt %, more preferably about 40 wt % to about 70 wt % of an organic solvent.

Polymeric Controlled Release Additive

The polymeric composition of the invention also includes a polymeric controlled release additive. The presence of a polymeric controlled release additive in the polymeric composition substantially reduces the "intitial burst" of biologically active agent released from the polymeric composition during the initial 24 hours after implantation. As used herein, the term "substantially reduces" means a decrease of at least 15% of biologically active agent released from the polymeric composition compared to a composition without the additive. Preferably, the polymeric controlled release additive reduces the initial burst of biologically active agent released from the polymeric composition by about 15% to about 70%, more preferably about 30% to about 60%, compared to a polymeric composition which does not include a controlled release additive.

According to the invention, the controlled release additive is a thermoplastic polymer having poly(lactide-co-glycolide) (PLG) moieties and polyethylene glycol (PEG) moieties. Preferably the controlled release additive is a PLG/PEG block copolymer which includes from about 50 mole % to about 90 mole % lactide monomers and about 50 mole % to about 10 mole % glycolide monomers. More preferably, the PLG/PEG block copolymer includes from about 50 mole % to about 75 mole % lactide monomers and about 50 mole % to about 25 mole % glycolide monomers. Preferably the PEG moiety has a molecular weight of about 1,000 Daltons to about 10,000 Daltons, more preferably about 5000 Daltons. The PEG portion of the block copolymer ranges from about 1 wt % to about 20 wt % of the total weight of the block copolymer. The percentage is dependent on the molecular weight of the block copolymer that is prepared and the molecular weight of the polyethylene glycol that is used. Thus, a block copolymer with a weight average molecular weight of 100,000 Daltons (I.V. approx. 0.8 dL/g) prepared with PEG having a molecular weight of 5,000 Daltons will contain about 5 wt % PEG. If PEG with a molecular weight of 1,000 Daltons is used, the block copolymer will include about 1 wt % of PEG.

The inherent viscosity (abbreviated as "I.V."; units are in deciliters/gram) of the polymeric controlled release additive is a measure of its molecular weight. Preferably, the inherent viscosity of the controlled release additive is from about 0.50 dL/g to about 1.0 dL/g (as measured in chloroform), more preferably from about 0.70 dL/g to about 0.90 dL/g.

Suitable polymeric controlled release additives include any PLG/PEG block copolymer with the previously mentioned attributes. Examples of suitable polymeric controlled release additives include 50/50 PLG/PEG-5000 (0.81); 70/30 PLG/PEG-5000 (0.73); and 70/30 PLG/PEG-5000 (0.79).

The polymeric controlled release additive is present in the polymeric composition in an amount effective to reduce the initial burst of biologically active agent released from the polymeric composition during the first 24 hours after implantation. Preferably, the polymeric composition includes about 1 wt % to about 50 wt %, more preferably about 2 wt % to about 20 wt % of the polymeric controlled release additive.

Biologically-Active Agent.

The polymeric composition also includes a biologically-active agent. Biologically-active agents which may be used alone or in combination in the polymer system include medicaments, drugs, or other suitable biologically-, physiologically-, or pharmaceutically-active substances capable of providing a local or systemic biological, physiological or therapeutic effect and of being released from the resulting matrix into adjacent or surrounding tissue fluids. Upon implantation, the biologically active agent becomes incorporated into the implant matrix. The biologically active agent is capable of being released from the matrix into the adjacent tissue fluid and to the pertinent body tissue or organ, either adjacent to or distant from the implant site, preferably at a controlled rate. The release of the biologically active agent from the matrix may be varied, for example, by the solubility of the biologically active agent in an aqueous medium, the distribution of the agent within the matrix, the size, shape, porosity and solubility and biodegradability of the solid matrix.

The biologically-active agent may be soluble in the polymeric composition, to form a homogeneous mixture, or insoluble in the polymer formulation to form a suspension or dispersion. Preferably, the polymer formulation includes the biologically-active agent in an amount effective to provide the desired level of biological, physiological, pharmacological and/or therapeutic effect in the animal. The amount of biologically active agent incorporated into the polymeric formulation depends upon the desired release profile, the concentration of biologically active agent required for a biological effect, and the length of time that the drug should be released for treatment. There is generally no critical upper limit on the amount of the biologically active agent that can be included in the polymeric composition. However, the biologically active agent should not be present in such a high concentration that the biologically active agent significantly alters the viscosity of the polymeric composition and interferes with its application to a patient's tissues. The lower limit of the amount of biologically active agent incorporated into the polymer formulation depends on the activity of the biologically active material and the period of time desired for treatment. Typically, the polymeric composition includes about 2 wt % to about 40 wt %, more preferably about 5 wt % to about 10 at % of a biologically active agent.

Examples of biologically active agents that are useful include substances capable of preventing an infection systemically in an animal or locally at the defect site, for example, anti-inflammatory agents such as hydrocortisone or prednisone; antibacterial agents such as penicillin, cephalosporins, bacitracin, tetracycline, doxycycline, gentamycin, quinolines, neomycin, clindamycin, kanamycin, or metronidazole; antiparasitic agents such as quinacrine, chloroquine, or vidarabine; antifungal agents such as nystatin; antiviral agents such as acyclovir, ribarivin, or interferons; analgesic agents such as salicylic acid, acetaminophen, ibuprofen, naproxen, piroxicam, flurbiprofen, or morphine; local anaesthetics such-as cocaine, lidocaine, bupivacaine, and benzocaine; immunogens (vaccines) for stimulating antibodies against hepatitis, influenza, measles, rubella, tetanus, polio, and rabies; peptides such as leuprolide acetate (an LH-RH agonist), nafarelin, or ganirelix.

Substances which are capable of promoting growth and survival of cells and tissues or augmenting the functioning of cells, or metabolic precursors thereof are also useful biologically active agents, for example, a nerve growth promoting substance such as a ganglioside or a nerve growth factor; a hard or soft tissue growth promoting agent such as fibronectin (FN), human growth hormone (HGH), a colony stimulating factor, bone morphogenic protein, platelet-derived growth factor (PDGP), insulin-derived growth factor (IGF-I, IGF-II), transforming growth factor alpha (TGF-α), transforming growth factor beta (TGF-β), epidermal growth factor (EGF), fibroblast growth factor (FGF), or interleukin-1 (IL-1); an osteoinductive agent or bone growth promoting substance such as bone chips, or demineralized freeze-dried bone material; antineoplastic agents such as methotrexate, 5-fluorouracil, floxuridine, adriamycin, vinblastine, cisplatin, tumor-specific antibodies conjugated to toxins or tumor necrosis factor (TNF).

Other useful substances include hormones such as progesterone, testosterone, and follicle stimulating hormone (FSH) (birth control, fertility enhancement), insulin, or somatotrophins; antihistamines such as diphenhydramine, or chlorphencramine; cardiovascular agents such as digitalis, nitroglycerine, papaverine, or streptokinase; anti-ulcer agents such as cimetidine hydrochloride, or isopropamide iodide; bronchodilators such as metaprotenal sulfate, or aminophylline; vasodilators such as theophylline, niacin or minoxidil; central nervous system agents such as a tranquilizer, β-adrenergic blocking agents, or dopamine; antipsychotic agents such as risperidone, olanzapine; narcotic antagonists such as naltrexone, naloxone or buprenorphine.

Polymeric Composition

The polymeric composition of the invention includes a base polymer, an organic solvent, a controlled release additive and a biologically active agent. According to the invention, the base polymer is a thermoplastic polymer that is soluble in the organic solvent and the organic solvent is miscible to dispersible in an aqueous medium, such as body or tissue fluids. Upon contact with an aqueous medium, the organic solvent diffuses or dissipates from the polymeric composition into the aqueous medium and the base polymer slowly precipitates or coagulates to form a solid matrix. The controlled release additive reduces the burst of biologically active agent released from the polymeric composition as it is coagulating to form the solid matrix or implant. The controlled release additive is preferably a PLG/PEG block copolymer.

The concentration of polymer (both the base polymer and the controlled release additive) in the polymeric composition may affect the rate at which the composition coagulates to form a matrix (e.g., a polymeric composition with a higher concentration of polymer may coagulate more quickly).

The percentage of polymer present in the composition may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances, for example. when applying the formulation via an aerosol spray.

Formation of a Polymer Matrix

In general, a solid implant or matrix is formed by dispensing the flowable polymeric composition either into a tissue or onto the surface of a tissue which is surrounded by an aqueous medium. The composition can be applied to a patient's tissues by any convenient technique, for example, by brushing, spraying, extruding, dripping, injecting, or painting.

Optionally, after the polymeric composition is applied to a tissue defect, an aqueous solution, such as a saline solution, can be applied over the polymeric composition to enhance coagulation of the thermoplastic polymer to form the matrix.

The Polymer Matrix

When the polymeric composition is applied to a tissue, the organic solvent slowly dissipates into the surrounding aqueous or body fluids and the substantially insoluble thermoplastic polymer precipitates or coagulates to form a polymer matrix. The polymeric controlled release additive reduces the initial burst of biologically active agent released from the polymeric composition as it coagulates to form a solid implant. Once the solid implant is formed, the biologically active agent is released from the implant by diffusion or dissolution from within the polymeric matrix and/or the biologically active agent is released as the matrix is biodegraded, bioeroded or bioabsorbed.

According to the invention, the resulting matrix is solid but is also able to conform with the irregular surface of the tissue.

The solid implant will slowly biodegrade within the body and will release the biologically active agent contained within its matrix at a controlled rate until depleted. With certain drugs, the polymer will degrade after the biologically active agent has been completely released. With other biologically active agents, such as peptides or proteins, the biologically active agent will be completely released only after the polymer has degraded to a point where the non-diffusing biologically active agent has been exposed to body or tissue fluids.

The solid matrix is capable of biodegradation, bioerosion and/or bioabsorption within the implant site of the animal. Generally, the implant matrix will breakdown over a period from about 1 week to about 12 months, preferably about 1 month to about 6 months.

WORKING EXAMPLES

The following examples demonstrate the ability of PEG block copolymers to reduce the initial burst of biologically active agent released from polymeric formulations.

EXAMPLE 1

The Initial Burst of Leuprolide Acetate From a Polymeric Formulation Made Using PLG/PEG-5000 as the Only Polymer This in vivo experiment was performed to measure the initial burst (release from the polymeric composition within the first twenty-four (24) hours of implantation) of a biologically active agent (Leuprolide Acetate) from a polymeric composition which included 70/30 PLG/PEG-5000 (0.73) as the only base polymer.

The following is an explanation of the notation used to designate the polymers used throughout the Working Examples: The PLG/PEG block copolymer included polyethylene glycol having a molecular weight of 5000 Daltons. This is designated by the following notation: PEG-5000. The PLG/PEG block copolymer was formed by combining the PEG with 70 mole % Lactide monomers and 30 mole % Glycolide monomers. This is designated by the following notation 70/30 PLG. The inherent viscosity of the PLG/PEG block copolymer was 0.73 dL/g and is designated (0.73).

One of skill in the art is familiar with methods of making block copolymers such as 70/30 PLG/PEG-5000 (0.73). Additionally, the 70/30 PLG/PEG-5000 block copolymer can be purchased from Birmingham Polymers, Inc., Birmingham, Ala.

A polymeric composition was formed which included 70/30 PLG/PEG-5000 (0.73) as the base polymer, dimethyl sulfoxide (DMSO) as an organic solvent and Leuprolide Acetate (LA) as a biologically active agent.

The PLG/PEG block copolymer and DMSO were weighed and combined in a glass jar to form a mixture having approximately 35 wt % polymer and 65 wt % solvent. The mixture was incubated on a shaker and gently agitated at room temperature until the polymer completely dissolved to form a clear flowable polymeric solution.

The LA was then combined with the flowable polymeric solution to form a flowable polymeric composition comprising about 3 wt % LA and about 97 wt % polymeric solution. The polymeric composition was incubated overnight at room temperature. The following day, the polymeric composition was mixed thoroughly using a glass stir rod and aspirated in a 1 cc syringe having a 21 gauge needle. 100 µl of the polymeric composition was injected subcutaneously into the dorsal region of five rats (i.e., 100 µl per rat).

The implants were retrieved 24 hours post-administration and analyzed for residual LA by reverse phase high performance liquid chromatography (RP-HPLC). Methods for such analysis are known to those of skill in the art. The amount of LA in the implant was compared to the amount of LA in the polymeric composition and recorded as the percent decrease of LA "lost" by the Initial Burst. The percent release for each implant was calculated and the values averaged to obtain a mean percent release.

The results are shown in Table 1, below. The data shows that the initial burst of LA released from the polymeric composition was 50%. This is a relatively high percentage of biologically active agent that is lost during the first 24 hours after implantation. Thus, PLG/PEG does not appear to provide a desirable "initial burst" of biologically active agent when used as the base polymer.

TABLE 1

Percentage of Leuprolide Acetate lost during the first 24 hours after implantation for a polymeric composition having PLG/PEG as the base polymer.

| Base Polymer | Solvent | Polymer/Solvent (%) | Initial Burst (%) |
| --- | --- | --- | --- |
| 70/30 PLG/PEG-5000 (0.73) | DMSO | 35 wt % PLG/PEG 65 wt % DMSO | 50 |

EXAMPLE 2

The Effect of PLG/PEG-5000 as an Additive on the Initial Burst of Leuprolide Acetate From Various Polymeric Formulations The initial burst of LA from various polymeric compositions (shown in Table 2, below) was tested with and without 70/30 PLG/PEG-5000 (0.73) as an additive.

Using the procedure described in Example 1, the base polymers were combined with solvent (DMSO), with and without 70/30 PLG/PEG-5000 (0.73) as an additive, in the amounts shown in Table 2 to form a polymeric solution.

A "male syringe" (Syringe A) was filled with the polymeric solution. A second "female syringe" (Syringe B) was filled with the biologically active agent, LA. Shortly prior to injection the two syringes were coupled and the contents were mixed by pushing the plungers back and forth to form a polymeric composition which comprised about 3 wt % LA and about 97 wt % polymeric solution. 100 µl of each polymeric composition was injected subcutaneously into the dorsal area of five rats using syringe A, which had a 21 gauge needle.

The resulting implants were retrieved 24 hours post administration and assayed for residual LA by RP-HPLC as described in Example 1. The results (the mean values) are shown in Table 2.

TABLE 2

Percentage of leuprolide acetate released 24 hours after subcutaneous injection in rats

| Polymer | Additive | Polymer/Solvent (%) | Initial burst (%) |
| --- | --- | --- | --- |
| 50/50 PLG 0.17) | — | 60 wt % PLG 40 wt % DMSO | 42 |
| 50/50 PLG (0.17) | 70/30 PLG/PEG-5000 (0.73) | 40 wt % PLG 10 wt % PLG/PEG 50 wt % DMSO | 16 |
| 85/15 PLG (0.27) | — | 50 wt % PLG 50 wt % DMSO | 50 |
| 85/15 PLG (0.27) | 70/30 PLG/PEG-5000 (0.73) | 40 wt % PLG 10 wt % PLG/PEG 50 wt % DMSO | 34 |
| 50/50 PLGH (0.4) | — | 30 wt % PLGH 70 wt % DMSO | 68 |
| 50/50 PLGH (0.4) | 70/30 PLG/PEG-5000 (0.73) | 30 wt % PLGH 5 wt % PLG/PEG 65 wt % DMSO | 59 |
| 50/50 PLGH (0.2) | — | 50 wt % PLGH 50 wt % DMSO | 47 |
| 50/50 PLGH (0.2) | 70/30 PLG/PEG-5000 (0.73) | 45 wt % PLGH 5 wt % PLG/PEG 50 wt % DMSO | 30 |

The results in Table 2 show that most of the polymer compositions without the additive had about the same initial burst as the composition of Example 1 (PLG/PEG as the base polymer). Surprisingly, the presence of 70/30 PLG/PEG-5000 (0.73) as an additive significantly decreases the initial burst of the biologically active agent released from a polymeric composition (to values of 16% to 34%).

EXAMPLE 3

The Effect of PLG/PEG-5000 on the Initial Burst of Floxuridine From Various Polymeric Formulations—in Vitro Experiments Floxuridine is an antineoplastic agent that has been used for chemotherapy of advanced adenocarcinomas of the gastrointestinal tract. A polymeric formulation that continuously administers floxuridine directly to the site of action over an extended period of time may provide better anti-tumor activity while reducing systemic toxicity.

Various polymeric compositions formulations were prepared using the same methods described in Example 1. Base polymers included polylactide/glycolide copolymers with hydroxy endgroups (PLG); polylactide glycolide copolymer with acid end groups (PLGH); and polylactic acid homopolymer with acid end groups (PLAH) (all three are available from Birmingham Polymers, Inc. Birmingham, Ala.). The polymeric compositions included the base polymer, an organic solvent (N-methyl-2-pyrrolidone "NMP"), and floxuridine. Floxuridine was added to each polymer solution to provide a final composition with 10 wt % floxuridine and 90 wt % polymer solution. The amounts of each constituent for the polymeric composition for each formulation is shown in Table 3, below.

An in vitro test of the initial burst was performed using fresh large eggs purchased from a local supermarket. About 50 µl of the polymeric composition was injected into each egg through a 26-gauge needle. Five eggs were injected with each composition. The eggs were then incubated for 24 hours in a 37° C. orbit shaker orbiting at 100 rpm. After 24 hours, all eggs were cracked open and the implants were collected.

The floxuridine content in the implants was analyzed by RP-HPLC. The percentage of drug released was calculated as described in Example 1, above.

As shown in Table 3, polymeric compositions which include 50/50 PLG/PEG- 5000 (0.81) as an additive show a substantial decrease of floxuridine released from the polymeric composition during the initial burst. The addition of 2 wt % to 5 wt % of 50/50 PLG/PEG-5000 (0.81) as an additive significantly decreases the initial burst of biologically active agent released from the polymeric implants. This reduction in the initial burst of biologically active agent released was seen for polymeric formulations which included 50/50 PLG having differing inherent viscosities (i.e., molecular weights). Additionaly, the reduction in initial burst was also seen when the polymeric formulation included acid end-capped polymers such as PLGH and PLAH.

TABLE 3

Percentage of floxuridine released in 24 hours after injection in eggs for formulations with and without 50/50 PLG/PEG-5000 (0.81)

| Base Polymer | Additive | Polymer/ Solvent (wt %) | Initial Burst (%) |
|---|---|---|---|
| 50/50 PLG (0.12) | — | 50 PLG 50 NMP | 91.5 |
| 50/50 PLG (0.12) | 50/50 PLG/PEG-5000 (0.81) | 47.5 PLG 2.5 PLG/PEG 50 NMP | 42.3 |
| 50/50 PLG (0.12) | 50/50 PLG/PEG-5000 (0.81) | 45 PLG 5 PLG/PEG 50 NMP | 33.8 |
| 50/50 PLG (0.16) | — | 50 PLG 50 NMP | 75.4 |
| 50/50 PLG (0.16) | 50/50 PLG/PEG-5000 (0.81) | 47.5 PLG 2.5 PLG/PEG 50 NMP | 24.4 |
| 50/50 PLG (0.16) | 50/50 PLG/PEG-5000 (0.81) | 45 PLG 5 PLG/PEG 50 NMP | 15.3 |
| 50/50 PLG (0.26) | — | 40 PLG 60 NMP | 40.3 |
| 50/50 PLG (0.26) | 50/50 PLG/PEG-5000 (0.81) | 38 PLG 2 PLG/PEG 60 NMP | 27.9 |
| 50/50 PLG (0.26) | 50/50 PLG/PEG-5000 (0.81) | 36 PLG 4 PLG/PEG 60 NMP | 23.4 |
| 50/50 PLGH (0.20) | — | 40 PLGH 60 NMP | 57.7 |
| 50/50 PLGH (0.20 | 50/50 PLG/PEG-5000 (0.81) | 36 PLGH 4 PLG/PEG 60 NMP | 38.3 |
| PLAH (0.20) | — | 40 PLAH 60 NMP | 54.4 |
| PLAH (0.20) | 50/50 PLG/PEG-5000 (0.81) | 38 PLAH 2 PLG/PEG 60 NMP | 36.2 |
| PLAH (0.20) | 50/50 PLG/PEG-5000 (0.81) | 36 PLAH 4 PLG/PEG 60 NMP | 33.7 |

EXAMPLE 4

The Effect of PLG/PEG5000 on the Initial Burst of Floxuridine From Various Polymeric Formulations—in Vivo Experiments An in vivo drug release experiment was performed to compare the initial burst of floxuridine from various polymeric compositions which included either (1) an additive having a PEG moiety; or (2) PLG/PEG block copolymer as an additive. Additives having a PEG moieity (without a PLG moiety) include PEG 400 monostearate (a homopolymer available from Stepan Company, Maywood, N.J.) and Pluronic® F127 (an ethylene oxide/propylene oxide copolymer, available from BASF Corporation, Parsippany, N.J.).

The polymeric compositions were prepared as described in Example 3, above, with 10 wt % floxuridine. The amounts of constituents in each polymeric solution are shown in Table 4, below.

About 50 $\mu$l of each composition was injected subcutaneously in the dorsal area of five rats using a 23-gauge needle. After 24 hours, the rats were terminated with $CO_2$ and the implants were carefully recovered. Floxuridine content in the implants was then analyzed by RP-HPLC as described above. The percentage of drug released was calculated as described above.

Table 4 shows the effect of 50/50 PEG/PLG-5000 (0.81) as additive on the initial burst of floxuridine from the polymeric implants. As predicted from the in vitro study in eggs (Example 3), a dramatic reduction in the amount of drug released was apparent for every polymeric composition assayed, although the in vivo data generally shows a higher percentage of biologically active agent released in the same period of time than the in vitro data.

Additives having a PEG moiety, in the absence of a PLG moiety (such as PEG-400 monstearate and Pluronic® F127) did not appear to have the same effect as PLG/PEG in reducing the initial burst of biologically active agent released from the implants.

TABLE 4

Percentage of floxuridine released in 24 hours after subcutaneous injection in rats for formulations with and without additives

| Base Polymer | Additive | Polymer/ Solvent (wt %) | Initial Burst (%) |
|---|---|---|---|
| 50/50 PLG (0.16) | PEG-400 Monostearate | 49 PLG 1 PEG-MS 50 NMP | 97.3 |
| 50/50 PLG (0.16) | 50/50 PLG/PEG-5000 (0.81) | 48 PLG 2 PLG/PEG 50 NMP | 60.0 |
| 50/50 PLG (0.16) | 50/50 PLG/PEG-5000 (0.81) | 46 PLG 4 PLG/PEG 50 NMP | 55.7 |
| 50/50 PLG (0.26) | Pluronic ® F127 | 38 PLG 2 Pluronic ® 60 NMP | 84.5 |
| 50/50 PLG (0.26) | 50/50 PLG/PEG-5000 (0.81) | 38 PLG 2 PLG/PEG 60 NMP | 45.3 |
| 50/50 PLG (0.26) | 50/50 PLG/PEG-5000 (0.81) | 36 PLG 4 PLG/PEG 60 NMP | 60.4 |
| 50/50 PLG (0.26) | — | 50 PLG 50 NMP | 71.1 |
| 50/50 PLG (0.26) | 50/50 PLG/PEG-5000 (0.81) | 47.5 PLG 2.5 PLG/PEG 50 NMP | 29.1 |
| 50/50 PLG (0.26) | 50/50 PLG/PEG-5000 (0.81) | 45 PLG 5 PLG/PEG 50 NMP | 36.1 |
| 50/50 PLG (0.35) | — | 40 PLG 60 NMP | 78.0 |
| 50/50 PLG (0.35) | 50/50 PLG/PEG-5000 (0.81) | 38 PLG 2 PLG/PEG 60 NMP | 44.4 |

EXAMPLE 5

The Effect of the PEG Moiety of the PLG/PEG Block Copolymer on the Initial Burst of a Biologically Active Agent From Various Polymeric Formulations The polymeric compositions shown in Table 5 were prepared using the methods described in Example 3. Floxuridine was included as 10 wt % in each of the polymeric compositions. About 50 µl of each polymeric composition was injected into five rats. After 24 hours, the rats were terminated and the implants removed. The amount of floxuridine released from the polymeric composition was measured as described in Example 3, above. The results are shown in Table 5, below.

The results indicate that the PEG moiety of the PLG/PEG block copolymer is important to the additive's ability to reduce the burst of release of biologically active agent. As shown in Table 5, polymeric compositions containing the same amount of a PLG polymer without the PEG-moiety did not show any reduction in the initial burst, even when the PLG polymer without the PEG-moiety had a molecular weight comparable to the PLG/PEG additive.

TABLE 5

Percentage of floxuridine released in 24 hours after subcutaneous injection in rats for polymeric compositions containing high Molecular Weight PLG as an additive

| Base Polymer | Additive | Polymer/ Solvent (Wt %) | Initial Burst (%) |
|---|---|---|---|
| 50/50 PLG (0.35) | — | 40 PLG (0.35) 60 NMP | 78.0 |
| 50/50 PLG (0.35) | 50/50 PLG (0.61) | 38 PLG (0.35) 2 PLG (0.61) 60 NMP | 89.0 |
| 50/50 PLG (0.35) | 50/50 PLG (0.70) | 38 PLG (0.35) 2 PLG (0.70) 60 NMP | 76.9 |
| 50/50 PLG (.0.35) | 50/50 PLG (1.03) | 38 PLG (0.35) 2 PLG (1.03) 60 NMP | 81.4 |
| 50/50 PLG (0.35) | 50/50 PLG/PEG-5000 (0.81) | 38 PLG (0.35) 2 PLG/PEG 60 NMP | 44.4 |

EXAMPLE 6

The Effect of the Molecular Weight of the PLG/PEG Block Copolymer in Reducing the Initial Burst of Biologically Active Agent Released From a Polymeric Composition.

The polymeric compositions shown in Table 6 were made using the methods described in Example 3. Floxuridine was included as 10 wt % of each polymeric composition. About 50 µl of each polymeric composition was injected into five rats. After 24 hours, the rats were terminated and the implants removed. The amount of floxuridine released from the polymeric composition was measured as described in Example 3, above. The results are shown in Table 6, below.

The burst-reducing ability of PLG/PEG appears to be related to the molecular weight of the PLG/PEG block copolymer. To reduce the initial burst of release of a biologically active agent, it appears that the molecular weight of the PEG/PLG block copolymer should be relatively high (IV≈0.80 dL/g).

When 5% of a PEG/PLG block copolymer having an inherent viscosity of 0.41 was incorporated into a polymeric solution which included PLG (0.26) as the main polymer, the initial release of biologically active agent actually increased from 78.0% to 83.8%.

Additionally, it appears that the burst-reducing ability of a PLG/PEG additive is not affected by the ratio of PLG to PEG.

TABLE 6

Percentage of floxuridine released in 24 hours after subcutaneous injection in rats for formulations containing different PLG-PEG's

| Base Polymer | Additive | Polymer/ Solvent (wt %) | Initial Burst (%) |
|---|---|---|---|
| 50/50 PLG (0.35) | — | 40 PLG 60 NMP | 78.0 |
| 50/50 PLG (0.35) | 50/50 PLG/PEG-5000 (0.41) | 38 PLG 2 PLG/PEG 60 NMP | 83.8 |
| 50/50 PLG (0.35) | 50/50 PLG/PEG-5000 (0.81) | 38 PLG 2 PLG/PEG 60 NMP | 44.4 |
| 50/50 PLG (0.26) | — | 50 PLG 50 NMP | 71.1 |
| 50/50 PLG (0.26) | 50/50 PLG/PEG-5000 (0.81) | 47.5 PLG 2.5 PLG/PEG 60 NMP | 29.1 |
| 50/50 PLG (0.26) | 70/30 PLG/PEG-5000 (0.79) | 47.5 PLG 2.5 PLG/PEG 60 NMP | 25.7 |
| 50/50 PLG (0.35) | 50/50 PLG/PEG-5000 (0.81) | 47.5 PLG 2.5 PLG/PEG 60 NMP | 27.4 |
| 50/50 PLG (0.35) | 70/30 PLG/PEG-5000 (0.79) | 47.5 PLG 2.5 PLG/PEG 60 NMP | 26.2 |

EXAMPLE 7

The Amount of PLG/PEG Block Copolymer Necessary to Reduce the Initial Burst of a Biologically Active Agent From Various Polymeric Formulations The polymeric compositions shown in Table 7 were made using the methods described in Example 3. Floxuridine was included in each polymeric composition at 10 wt %. About 50 µl of each polymeric composition was injected into five rats. After 24 hours, the rats were terminated and the implants removed. The amount of floxuridine released from the polymeric composition was measured as described in Example 3, above. The results are shown in Table 7, below.

The amount of PLG/PEG block copolymer added to the polymeric composition appears to affect the reduction in initial burst of release of biologically active agent. The optimum amount at which maximum burst reduction is achieved is from about 1% to about 5%. For the polymeric composition in this experiment, the optimum amount is about 2.5% percent of the total polymer amount in the polymeric composition (Table 7). It is possible that such optimum amount may vary for different polymers or different biologically active agents used in a given formulation depending upon the hydrophilicity of the base polymer or biologically active agent, the molecular weight of the base polymer, and diffusion characteristics of the biologically active agent within the polymeric matrix.

TABLE 7

Percentage of floxuridine released in 24 hours after subcutaneous injection in rats for formulations containing varied amounts of PLG/PEG-5000 (0.81)

| Base Polymer | Additive | Polymer/Solvent (wt %) | Initial Burst (%) |
|---|---|---|---|
| 50/50 PLG (0.26) | — | 50 PLG<br>50 NMP | 71.1 |
| 50/50 PLG (0.26) | 50/50 PLG/PEG-5000 (0.81) | 49 PLG<br>1 PLG/PEG<br>50 NMP | 43.9 |
| 50/50 PLG (0.26) | 50/50 PLG/PEG-5000 (0.81) | 47.5 PLG<br>2.5 PLG/PEG<br>50 NMP | 29.1 |
| 50/50 PLG (0.26) | 50/50 PLG/PEG-5000 (0.81) | 45 PLG<br>5 PLG/PEG<br>50 NMP | 36.1 |

EXAMPLE 8

The Effect of PLG/PEG Block Copolymer on the Initial Burst of a Local Anesthetic From Various Polymeric Formulations The polymeric compositions shown in Table 8 were formed using the method described in Example 3. 10% (w/w) of a local anesthetic (either Lidocaine Base or Lidocaine HCl) was included in each polymeric composition.

About 100 μl of each polymeric composition was injected intramuscularly (IM) into the hind leg of five rats. The implants were retrieved after 24 hours and analyzed for drug content by RP-HPLC. The results shown in Table 8 demonstrate that the PLG/PEG additive reduces the initial burst of both biologically active agents. A more dramatic reduction is obtained with the more hydrophilic hydrochloride form of the drug.

TABLE 8

Percentage of Anesthetic released in 24 hours after intramuscular injections in rats for formulation with and without 50/50 PLG/PEG-5000 (0.81)

| Base Polymer | Additive | Drug | Polymer/Solvent (wt %) | Initial Burst (%) |
|---|---|---|---|---|
| 65/35 PLG (0.23) | — | Lidocaine Base | 40 PLG<br>60 NMP | 54.0 |
| 65/35 PLG (0.23) | 50/50 PLG/PEG-5000 (0.81) | Lidocaine Base | 35 PLG<br>5 PLG/PEG<br>60 NMP | 46.0 |
| 75/25 PLG (0.20) | — | Lidocaine Base | 40 PLG<br>60 NMP | 70.0 |
| 75/25 PLG (0.20) | 50/50 PLG/PEG-5000 (0.81) | Lidocaine Base | 35 PLG<br>5 PLG/PEG<br>60 NMP | 57.0 |
| 50/50 PLGH (0.30) | — | Lidocaine HCl | 40 PLGH<br>60 NMP | 63.0 |
| 50/50 PLGH (0.30) | 50/50 PLG/PEG-5000 (0.81) | Lidocaine HCl | 35 PLGH<br>5 PLG/PEG<br>60 NMP | 30.0 |
| 65/35 PLG (0.23) | — | Lidocaine HCl | 40 PLG<br>60 NMP | 82.0 |
| 65/35 PLG (0.23) | 50/50 PLG/PEG-5000 (0.81) | Lidocaine HCl | 35 PLG<br>5 PLG/PEG<br>60 NMP | 30.0 |

What is claimed is:

1. A polymeric composition for forming a controlled release implant within a body, comprising:
    a biocompatible, biodegradable, thermoplastic base polymer that is insoluble in aqueous or body fluids;
    a biocompatible, organic solvent that is soluble in aqueous or body fluid;
    a poly(lactide-co-glycolide)/polyethylene glycol block copolymer; and
    a biologically active agent
    wherein the polymeric composition is capable of forming the controlled release implant by dissipation or dispersement of the organic solvent within the body.

2. The polymeric composition of claim 1, wherein the poly(lactide-co-glycolide)/polyethylene glycol block copolymer includes from about 50 mole % to about 90 mole % lactide monomers and about 50 mole % to about 10 mole % glycolide monomers.

3. The polymeric composition of claim 1, wherein the organic solvent is selected from the group consisting of substituted heterocyclic compounds, esters of carbonic acid and alkyl alcohols, alkyl esters of monocarboxylic acids, alkyl esters of dicarboxylic acids, alkyl esters of tricarboxylic acids, alkyl ketones, alcohols, dialkylamides, dimethylsulfoxide (DMSO), dimethylsulfone, tetrahydrofuran, lactones, cyclic alkyl amides, aromatic amides, mixtures and combinations thereof.

4. The polymeric composition of claim 3, wherein the poly(lactide-co-glycolide)/polyethylene glycol block copolymer has an inherent viscosity from about 0.50 dL/g to about 1.00 dL/g.

5. A polymeric composition for forming a controlled release implant within a body, comprising:
    a biocompatible, biodegradable, thermoplastic base polymer that is insoluble in aqueous or body fluids;
    a biocompatible, organic solvent that is soluble in aqueous or body fluid;
    a polymeric controlled release additive that is insoluble in aqueous or body fluids and is a block copolymer of a biocompatible, biodegradable, thermoplastic polymer and polyethylene glycol; and
    a biologically active agent;
    wherein the base polymer, controlled release additive and solvent form a solution and the polymeric composition is capable of forming the controlled release implant by dissipation or dispersement of the organic solvent within the body.

6. A polymeric composition for forming a controlled release implant within a body, comprising:
    a biocompatible, biodegradable, thermoplastic base polymer that is insoluble in aqueous or body fluids;
    a biocompatible, organic solvent that is soluble in aqueous or body fluid;
    a polymeric controlled release additive that insoluble in aqueous or body fluid and is a block copolymer of a biocompatible, biodegradable, thermoplastic polymer and polyethylene glycol; and
    lidocaine HCl
    wherein the base polymer, controlled release additive and solvent form a solution and the polymeric composition is capable of forming the controlled release implant by dissipation or dispersement of the organic solvent within the body.

7. A polymeric composition for forming a controlled release implant within a body, comprising:
- a biocompatible, biodegradable, thermoplastic base polymer that is insoluble in aqueous or body fluids;
- a biocompatible, organic solvent that is soluble in aqueous or body fluid;
- a polymeric controlled release additive that insoluble in aqueous or body fluid and is a block copolymer of a biocompatible, biodegradable, thermoplastic polymer and polyethylene glycol; and
- floxuridine wherein the base polymer, controlled release additive and solvent form a solution and the polymeric composition is capable of forming the controlled release implant by dissipation or dispersement of the organic solvent within the body.

8. A polymeric composition for forming a controlled release implant within a body, comprising:
- a biocompatible, biodegradable, thermoplastic base polymer that is insoluble in aqueous or body fluids;
- a biocompatible, organic solvent that is soluble in aqueous or body fluid;
- a polymeric controlled release additive that is insoluble in aqueous or body fluid and is a block copolymer of a biocompatible, biodegradable, thermoplastic polymer and polyethylene glycol; and
- leuprolide acetate wherein the base polymer, controlled release additive and solvent form a solution and the polymeric composition is capable of forming the controlled release implant by dissipation or dispersement of the organic solvent within the body.

9. A method of forming a controlled release implant in situ within a body, comprising:
- placing a polymeric composition into an implant site within the body, wherein the polymeric composition comprises a biocompatible, biodegradable, thermoplastic base polymer that is insoluble in aqueous or body fluids; a biocompatible, organic solvent that is soluble in aqueous or body fluid; a poly(lactide-co-glycolisde)/polyethylene glycol block copolymer; and a biologically active agent, wherein the polymeric composition is capable of forming the controlled release implant by dissipation or dispersement of the organic solvent within the body.

10. The method of claim 9, wherein the poly(lactide-co-glycolide)/polyethylene glycol block copolymer includes from about 50 mole % to about 90 mole % lactide monomers and about 50 mole % to about 10 mole % glycolide monomers.

11. The method of claim 9, wherein the poly(lactide-co-glycolide)/polyethylene glycol block copolymer has an inherent viscosity from about 0.50 dL/g to about 1.00 dL/g.

12. A method of forming a controlled release implant in situ within a body, comprising:
- placing a polymeric composition into an implant site within the body, wherein the polymeric composition comprises a biocompatible, biodegradable, thermoplastic base polymer that is insoluble in aqueous or body fluids; a biocompatible, organic solvent that is soluble in aqueous or body fluid; a poly(lactide-co-glycolisde)/polyethylene glycol block copolymer; and a biologically active agent selected from the group consisting of lidocaine base, lidocaine HCl, floxuridine, and leuprolide acetate, wherein the polymeric composition is capable of forming the controlled release implant by dissipation or dispersement of the organic solvent within the body.

13. A method of forming a controlled release implant in situ within a body, comprising:
- placing a polymeric composition into an implant site within the body, wherein the polymeric composition comprises a biocompatible, biodegradable, thermoplastic base polymer that is insoluble in aqueous or body fluids; a biocompatible, organic solvent that is soluble in aqueous or body fluid; a polymeric controlled release additive that is insoluble in aqueous or body fluids and is a block copolymer of a biocompatible, biodegradable, thermoplastic polymer and polyethylene glycol; and a biologically active agent, wherein the base polymer, controlled release additive and solvent form a solution and the polymeric composition is capable of forming the controlled release implant by dissipation or dispersement of the organic solvent within the body.

* * * * *

UNITED STATES PATENT AND TRADEMARK OFFICE
CERTIFICATE OF CORRECTION

PATENT NO. : 6,630,155 B1
DATED : October 7, 2003
INVENTOR(S) : Richard L. Dunn et al.

It is certified that error appears in the above-identified patent and that said Letters Patent is hereby corrected as shown below:

Column 6,
Line 36, delete "at %" and insert -- wt % -- therefor.

Column 7,
Line 48, delete "." after "example" and insert -- , -- therefor.

Column 17,
Line 42, delete "glycolisde" and insert -- glycolide -- therefor.

Column 18,
Line 18, delete "glycolisde" and insert -- glycolide -- therefor.

Signed and Sealed this

Twenty-fourth Day of February, 2004

JON W. DUDAS
*Acting Director of the United States Patent and Trademark Office*